United States Patent [19]

Ono et al.

[11] Patent Number: 4,774,319
[45] Date of Patent: Sep. 27, 1988

[54] SYNTHESIS OF A DERIVATIVE OF GRF AND INTERMEDIATE PEPTIDES

[75] Inventors: Keiichi Ono; Yoshiyuki Kai; Yoshiaki Takebayashi; Akihiko Sano; Kazushi Suwa, all of Takarazuka, Japan

[73] Assignee: Sumitomo Pharmaceuticals Company, Limited, Osaka, Japan

[21] Appl. No.: 119,279

[22] Filed: Nov. 9, 1987

Related U.S. Application Data

[63] Continuation of Ser. No. 832,893, Feb. 26, 1986, abandoned.

[30] Foreign Application Priority Data

Mar. 6, 1985 [JP] Japan ................................. 60-44370
Dec. 11, 1985 [JP] Japan ............................. 60-279682

[51] Int. Cl.$^4$ ......................... C07K 7/06; C07K 7/08; C07K 7/10
[52] U.S. Cl. ................................. 530/324; 530/326; 530/325; 530/327; 530/328; 530/329
[58] Field of Search ............... 530/324, 325, 326, 327, 530/328, 329

[56] References Cited

U.S. PATENT DOCUMENTS 4,581,168  4/1986  Diaz et al. ........................... 530/337

FOREIGN PATENT DOCUMENTS 24774    2/1984  Australia .
61-115098  2/1986  Japan .

OTHER PUBLICATIONS

Nature, 300, pp. 276–278 (1981).
Chem. Pharm. Bull., 32, pp. 510–519 (1984).
Chem. Pharm. Bull., 32, pp. 520–529 (1984).
J. Takeda Res. Lab., 42, pp. 209–226 (1983).
Peptide Chemistry, pp. 285–290 (1983).
Int. J. Peptide Protein Res., 24, pp. 498–504 (1984).

Primary Examiner—Delbert R. Phillips
Attorney, Agent, or Firm—Stevens, Davis, Miller & Mosher

[57] ABSTRACT

A process for the manufacture of a polypeptide (I) having the formula:

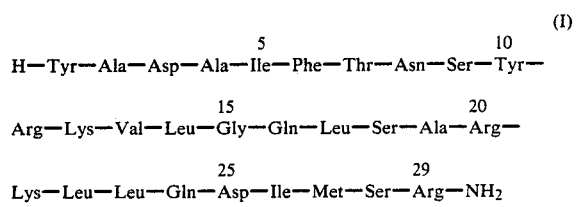

which comprises steps of:
(a) coupling, successively and in the order of the sequence of the polypeptide (I), the four protected fragments A, B, C and D or five protected fragments A, B, C, E and F,
said fragment A by the formula, Leu-Gln-Asp-Ile-Met-Ser-Arg-NH$_2$
said fragment B by the formula, Gln-Leu-Ser-Ala-Arg-Lys-Leu
said fragment C by the formula, Arg-Lys-Val-Leu-Gly
said fragment D by the formula, Tyr-Ala-Asp-Ala-Ile-Phe-Thr-Asn-Ser-Tyr
said fragment E by the formula, Ile-Phe-Thr-Asn-Ser-Tyr
and said fragment F by the formula, Tyr-Ala-Asp-Ala
being represented, respectively, and
(b) eliminating, at the end of sequence, all the protecting groups to provide the polypeptide (I) which is active on the stimulation of the release of the growth hormone and thus is very useful as medicine for treatment of growth hormone deficiency disease and the like.

9 Claims, No Drawings

SYNTHESIS OF A DERIVATIVE OF GRF AND INTERMEDIATE PEPTIDES

CROSS-REFERENCE TO RELATED APPLICATIONS

This application is a continuation of application Ser. No. 832,893 filed Feb. 26, 1986, now abandoned.

The present invention relates to a process for the manufacture of a polypeptide (I) having the formula:

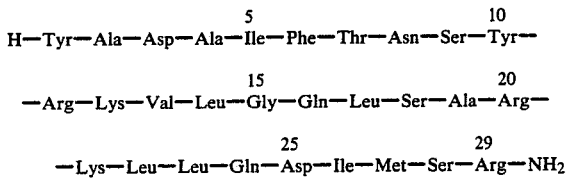

This peptide is a derivative of growth hormone releasing factor (GRF).

This peptide is active on the stimulation of the release of the growth hormone (GH). The therapeutic interest of this substance in human medicine will therefore lie in the treatment of growth hormone deficiency disease (dwarfism etc.). Other applications are possible in the treatment of ulcers, repair of wounds, etc.

In the veterinary domain, the interest of this compound in the weight growth of farm-breeding animals and in the increase in lactation is obvious.

This peptide is already synthesized by solid phase method (Nature, 300, 276 (1982)). Conventional processes of synthesis in solid phase allow small quantities of this active principle to be prepared in short periods of time, but at very high costs which are incompatible with a large-scale pharmaceutical development.

The industrial development of this peptide necessitated the synthesis of large quantities of this compound. The present invention describes a process of synthesis in liquid phase which may be carried out on an industrial scale, allowing access to the active principle with excellent yield and rate of purity. This process is based on the principle of synthesis by fragment condensation method.

The fragment condensation method is an excellent method because the product having high purity is obtained by a simple purification in this method. Success in the fragment condensation method depends to a great extent on the judicious choice of the fragment.

The process of the present invention is characterized by the step of coupling, successively and in the order of the sequence of the polypeptide (I), the protected fragments which are possessed of the good solubility for the solvent and the good reactivity. That is to say, the step of the coupling, successively and in the order of the sequence of the polypeptide (I), four protected fragments A, B, C and D or five protected fragments A, B, C, E and F, said fragment A by the formula, Leu-Gln-Asp-Ile-Met-Ser-Arg-NH₂
said fragment B by the formula, Gln-Leu-Ser-Ala-Arg-Lys-Leu
said fragment C by the formula, Arg-Lys-Val-Leu-Gly
said fragment D by the formula, Tyr-Ala-Asp-Ala-Ile-Phe-Thr-Asn-Ser-Tyr
said fragment E by the formula, Ile-Phe-Thr-Asn-Ser-Tyr and said fragment F by the formula, Tyr-Ala-Asp-Ala being represented, respectively, is a characteristic of the present invention.

The coupling methods used in the present invention are azide method, oxidation-reduction method, diphenylphosphoryl azide method, carbodiimide method in the presence of additive, etc. The preferred coupling method for the synthesis of large quantities of polypeptide (I) is the carbodiimide method in the presence of additive from the viewpoint of hereinafter:

(1) operations are very simple.
(2) it is not necessary to cool the reaction mixtures.
(3) since side reactions are rarely found, it is possible to obtain the products having high purity by a simple purification.

The example of fragment condensation with carbodiimide method in the presence of additive is the following. Two protected fragments (one protected fragment in which the α-carboxyl group of C-terminal amino acid is not protected and the other functional groups are protected, another protected fragment in which the α-amino group of N-terminal amino acid is not protected and the other functional groups are protected) are dissolved in an appropriate solvent, and a carbodiimide reagent and an additive are added. Then the reaction mixture is stirred and if necessary the pH of the reaction mixture can be maintained at mild alkaline by addition of an appropriate base.

Examples of the carbodiimide reagents are N,N'-dicyclohexyl carbodiimide (DCC), 1-ethyl-3-(3-dimethylaminopropyl)-carbodiimide, 1-ethyl-3-(3-dimethylaminopropyl)-carbodiimide hydrochloride, etc.

Examples of additives, which are used in the carbodiimide method in the presence of additive, are N-hydroxysuccinimide (HOSu), 1-hydroxybenzotriazole (HOBt), N-hydroxy-5-norbornene-2,3-dicarboximide (HONB), etc.

Examples of the solvents are dimethylsulfoxide, dimethylformamide, hexamethylphosphoramide, dioxane, tetrahydrofuran, N-methylpyrolidone, etc.

The coupling is carried out at temperatures of −20° to 40° C.

The deprotecting methods used in the present invention are well known in the peptide art. Examples of deprotecting methods are: (1) deprotection by acids, such as trifluoroacetic acid, methane sulfonic acid, p-toluene sulfonic acid, formic acid, hydrogen bromide in acetic acid, trifluoromethane sulfonic acid, anhydrous hydrogen fluoride; (2) reductive methods, such as hydrogenolysis in the presence of catalyst (Pd, Pd/C, Pt, etc.), Na in liquid ammonia, Zn in acetic acid.

The preferred deprotecting reagent used in the selective elimination of the α-amino protecting group throughout the chain building is p-toluenesulfonic acid, or methanesulfonic acid, or trifluoro acetic acid. On the other hand the preferred deprotecting reagent used in the final deprotection of all the protecting groups is trifluoromethanesulfonic acid or anhydrous hydrogen fluoride.

When using acidic reagents for cleaving, cation scavenagers (such as anisole, phenol, thioanisole, thiophenol, cresole, methyl ethyl sulfide) can be added to the reaction mixture.

The deprotecting reaction is carried out at temperatures of −40° to 40° C.

The amino protecting groups used in the present invention are tosyl, benzyloxycarbonyl (Z), t-butyloxycarbonyl (Boc), trityl, p-methoxybenzyloxycarbonyl (PMZ), formyl, trifluoroacetyl, o-Nitrophenylsulphenyl, 3-nitro-2-pyridinesulphenyl, etc. The preferred α-amino protecting group is Boc or PMZ. The preferred ε-amino protecting group of lysine is Z.

The carboxyl protecting groups used in the present invention are well known in the peptide art. Examples of the carboxyl protecting groups are lower alkyl esters (such as methyl ester, ethyl ester, isopropyl ester, t-butyl ester, cyclopentyl ester, cyclohexyl ester (OcHex)), benzyl ester (OBzl), p-methoxybenzyl ester, p-nitrobenzyl ester, phenacyl ester (OPac), etc. The preferred α-carboxyl protecting group is phenacyl ester or benzyl ester. The preferred carboxyl protecting group of side chain of aspartic and glutamic acids is benzyl ester or cyclohexyl ester.

The guanidine protecting groups of arginine are nitro, tosyl, benzyloxycarbonyl, adamantyloxycarbonyl, isobornyloxycarbonyl, mesitylene-2-sulfonyl (Mts), etc. The preferred guanidine protecting group is Mts.

The protection of hydroxyl function of serine, threonine and tyrosine are not always necessary. But if necessary, the conventional protecting groups of hydroxy function (such as acetyl, benzyl, 2,6-dichlorobenzyl, benzyloxycarbonyl, t-butyl) are used.

The methionine is protected as methionine sulfoxide, if necessary.

The polypeptide (I), after the terminal deprotection, is purified by the conventional technique (such as ion exchanger chromatography, partition chromatography, gel filtration chromatography, reverse phase liquid chromatography).

The polypeptide (I) synthesized by this method is active on the stimulation of the release of the GH in rats (in vivo, in vitro).

The synthesis of the protected fragment A, B, C, D, E and F used in the present invention is carried out with the aid of conventional methods for peptide synthesis which are described in M. Bodansky & M. A. Ondetti "Peptide Synthesis" (*Interscience,* New York, 1966), F. M. Finn & K. Hofmann "The Proteins" 2 (Academic Press Inc., New York, 1976), Nobuo Izumiya et al. "peputido gosei" (Maruzen 1975) etc.

Practical and presently preferred embodiments of the invention are illustratively shown in the following examples without limiting the scope of the invention in any way.

The following abbreviations will be used.

The amino acids are represented by the symbols recommended by the Nomenclature Commission of the IUPAU-IUB, Biochemistry Section.

Ala: Alanine, Arg: Arginine
Asn: Asparagine, Asp: Aspartic acid
Gln: Glutamine, Glu: Glutamic acid
Gly: Glycine, Ile: Isoleucine
Leu: Leucine, Lys: Lysine
Met: Methionine, Phe: Phenylalanine
Ser: Serine, Thr: Threonine
Tyr: Tyrosine, Val: Valine With the exception of glycine, they all have the L-configuration PMZ: p-methoxybenzyloxycarbonyl
Boc: t-butyloxycarbonyl
Mts: mesitylene-2-sulfonyl
ONp: p-nitrophenol ester
Bzl: benzyl
OSu: N-hydroxysuccinimide ester
OPac: phenacyl ester
OcHex: cyclohexyl ester
Z: Benzyloxycarbonyl
TFA: trifluoroacetic acid
TosOH: p-toluenesulfonic acid
HOBt: 1-hydroxybenzotriazole
SBCF: sec-butylchloroformate
DCHA: dicyclohexylamine
NMM: N-methylmorpholine
$Et_3N$: triethylamine
CHA: cyclohexyl amine
DCC: dicyclohexylcarbodiimide
WSC: 1-ethyl-3-(3-dimethylaminopropyl)-carbodiimide
MeOH: methanol
THF: tetrahydrofuran
EtOH: ethanol
DMF: N,N-dimethylformamide
DMSO: dimethylsulfoxide
$AcONH_4$: ammonium acetate
HONB: N-hydroxy-5-norbornene-2,3-dicarboximide
TFMSA: trifluoromethanesulfonic acid
HPLC: high performance liquid chromatography
MSA: methanesulfonic acid
$CH_3CN$: acetonitrile
AcOEt: ethyl acetate
IPE: diisopropyl ether

EXAMPLE I

Synthesis of Boc-Leu-Gln-Asp(OBzl)-Ile-Met(O)-Ser(Bzl)-Arg(Mts)-$NH_2$ (AP-7)

1. Boc-Arg(Mts)-$NH_2$ (AP-1)

Boc-Arg(Mts)-OH prepared from 1.3 kg of Boc-Arg(Mts)-OH·CHA are dissolved at ambient temperature in 6.2 kg of THF, and 280 g of NMM are added. To this solution 380 g of SBCF are added at −10° C., and stirring is continued at −10° C. for 15 minutes, and then 0.69 kg of 29% aqueous ammonia are added at −10° C. The medium is stirred at −10° C. for 30 mins. and then at 5° C., and the development of the reaction is followed by HPLC. The reaction is terminated after 30 mins. The medium is poured into 31.5 kg of water, and then 19.2 kg of AcOEt are added. After stirring for 15 mins, the organic phase is washed by:

0.5N hydrochloric acid
an 8% aqueous solution of sodium bicarbonate
a 25% aqueous solution of sodium chloride The organic phase is dried over $MgSO_4$ and filtered. The filterate is evaporated to dryness at a temperature lower than 50° C. The residual oil is dissolved in 3.6 kg of acetonitrile and evaporated to dryness at a temperature lower than 50° C. (3 times). The oily AP-1 is obtained.

Yield: 1.00 kg (93.8%)

2. Boc-Ser(Bzl)-Arg(Mts)-$NH_2$ (AP-2)

970 g of AP-1 are dissolved in 7.5 kg of acetonitrile at ambient temperature, then 3.94 kg of p-toluene sulfonic acid-monohydrate are added at 15° C. The medium is stirred at 15° C. and the development of the reaction is followed by HPLC. The reaction is terminated after 3 hrs. Then to this solution are successively added at 5° C.:

1.89 kg of $Et_3N$
380 g of HOBt
730 g of Boc-Ser(Bzl)-OH
380 g of WSC

The reaction mixture is stirred at 5° C. for 1 hr, then at 25° C. The development of the reaction is followed by HPLC. After 3 hrs, the reaction is terminated. The reaction mixture is poured into 33 l of water, and then 36 kg of AcOEt are added. After stirring for 15 mins, the organic phase is washed by:

a 5% aqueous solution of citric acid
an 8% aqueous solution of sodium bicarbonate
a 25% aqueous solution of sodium chloride The organic phase is dried over MgSO$_4$ and filtered. The filtrate is evaporated to dryness at a temperature lower than 50° C. The residual oil is dissolved in 5.9 kg of acetonitrile and evaporated to dryness at a temperature lower than 50° C. (3 times). 1.21 kg of oily product are obtained.

Yield: 89.8%

3. Boc-Met(O)-Ser(Bzl)-Arg(Mts)-NH$_2$ (AP-3)

From 1.18 kg of AP-2 in 6.5 kg of acetonitrile, 3.53 kg of p-toluene sulfonic acid monohydrate, 1.70 kg of Et$_3$N, 350 g of HOBt·monohydrate, 590 g of Boc-Met-(O)OH and 350 g of WSC, 1.41 kg (96.9%) of oily AP-3 are obtained by employing the operational conditions described in Example I-2.

4. Boc-Ile-Met(O)-Ser(Bzl)-Arg(Mts)-NH$_2$(AP-4)

1.40 kg of AP-3 are dissolved in 6.3 kg of acetonitrile at ambient temperature, then 3.41 kg of p-toluene sulfonic acid·monohydrate are added at 15° C. The medium is stirred at 15° C. and the development of the reaction is followed by HPLC. The reaction is terminated after 3 hrs. To this solution are successively added at 5° C.: 1.64 kg of Et$_3$N, 335 g of HOBt·monohydrate, 513 g of Boc-Ile-OH, 335 g of WSC.

The reaction mixture is stirred at 5° C. for 1 hr, then at 25° C. The development of the reaction is followed by HPLC. After 3 hrs, the reaction is terminated. The reaction mixture is poured into 64 kg of a 15% aqueous solution of sodium chloride, then 43 kg of AcoEt are added. After stirring for 15 mins., the organic phase is washed with a 15% aqueous solution of sodium chloride. The organic phase is concentrated at a temperature lower than 50° C. The residue is taken up in 2.4 kg of MeOH and the product is precipitated by addition of 24 kg of IPE. It is filtered and washed with IPE (2.6 kg×2) and dried. This product must be washed again with 23 kg of AcOEt with stirring for 1 hr at 60° C. The solid is drained, washed with AcOEt (2.4 kg×2) and dried.

Yield: 1.40 kg (87.4%), m.p.: 153.5–161° C.
$[\alpha]_D^{20} = -5.4°$ (C=1, DMF)

5. Boc-Asp(OBzl)-Ile-Met(O)-Ser(Bzl)-Arg(Mts)-NH$_2$ (AP-5)

1.38 kg of AP-4 are suspended in 5.37 kg of acetonitrile at ambient temperature, then 2.93 kg of p-toluene sulfonic acid·monohydrate are added at 15° C. The medium is stirred at 15° C. and the development of the reaction is followed by HPLC. The reaction is terminated after 3 hrs. To this solution are successively added at 5° C.: 1.40 kg of Et$_3$N, 0.95 kg of DMSO, 263 g of HOBt·monohydrate, 548 g of Boc-Asp(OBzl)-OH, 263 g of WSC.

The medium is stirred at 5° C. for 1 hr, then at 25° C. The development of the reaction is followed by HPLC. After 3 hrs, the reaction is terminated. The reaction mixture is poured into 53 kg of water. After stirring for 30 mins, the precipitate formed is filtered and washed with water (21 kg×3) and dried. This product is washed again with 12.3 kg of AcoEt and 10 kg of IPE with stirring for 1 hr at ambient temperature. The solid is drained, washed with IPE (2 kg×2) and dried.

Yield: 1.64 kg (97.0%), m.p.: 171–185° C.
$[\alpha]_D^{20} = -13.7°$ (C=1, DMF)

6. Boc-Gln-Asp(OBzl)-Ile-Met(O)-Ser(Bzl)-Arg(Mts)-NH$_2$ (AP-6)

1.61 kg of AP-5 are suspended in 5.2 kg of acetonitrile at ambient temperature, then 2.79 kg of p-toluene sulfonic acid·monohydrate are added at 15° C. The reaction mixture is stirred at 15° C. and the development of the reaction is followed by HPLC. The reaction is terminated after 3 hrs. To this solution are successively added at 5° C.: 1.63 kg of Et$_3$N, 12 kg of DMSO, 264 g of HOBt·monohydrate, 649 g of Boc-Gln-ONp.

The medium is stirred at ambient temperature for 2 hrs. (the end of the reaction is determined by HPLC). The medium is poured into 110 kg of water. The precipitate obtained is filtered and washed with water (26 kg×3) and dried. This product is washed again with 32.4 kg of AcOEt with stirring for 1 hr at ambient temperature. The solid is drained, washed with AcOEt (3.24 kg×3) and dried.

Yield: 1.64 kg (90.9%), m.p.: 189–195° C
$[\alpha]_D^{20} = -12.2°$ (C=1, DMSO)

7. Boc-Leu-Gln-Asp(OBzl)-Ile-Met(O)-Ser(Bzl)-Arg(Mts)-NH$_2$ (AP-7)

1.54 kg of AP-6 are suspended in 6.5 kg of acetonitrile at ambient temperature, then a solution of 2.41 kg of methane sulfonic acid in 3.27 kg of acetonitrile are added at 10° C. The reaction mixture is stirred at 5° C. and the development of the reaction is followed by HPLC. The reaction is terminated after 1 hr 30 mins. To this solution are successively added at 5° C.: 6.7 kg of DMSO, 2.41 kg of Et$_3$N, 230 g of HOBt·monohydrate, 376 g of Boc-Leu-OH·monohydrate, 230 g of WSC.

The reaction mixture is stirred at 5° C. for 1 hr, then at 25° C. The development of the reaction is followed by HPLC. After 3 hrs, the reaction is terminated. The reaction mixture is poured into 85 kg of water. After stirring for 30 mins, the precipitate formed is filtered and washed with water (17 kg×3) and dried. This product is washed again with 28.4 kg of acetonitrile with stirring for 1 hr at ambient temperature. The solid is drained, washed with acetonitrile (5.7 kg×3) and dried.

Yield: 1.56 kg (92.7%), m.p.: 222–225° C.
$[\alpha]_D^{20} = -12.3°$ (C=1, DMSO)

8. Boc-Leu-Gln-Asp(OBzl)-Ile-Met(O)-Ser(Bzl)-Arg(Mts)-NH$_2$ (AP-7)

AP-7 is obtained by employing the same technique described in Japanese Patent (Appln. 84 236966).

EXAMPLE II

Synthesis of Boc-Gln-Leu-Ser(Bzl)-Ala-Arg(Mts)-Lys(Z)-Leu-OH (BC−7)

1. Boc-Lys(Z)-Leu-Opac (BP−2)

(A) 21.7 g of Boc-Lys(Z)-OH are dissolved in 100 ml of AcOEt, 5.76 g of NMM, then 7.81 g of SBCF are added at −10° C. The reaction mixture is stirred for 15 mins. To this mixture, a solution of 20.0 g of tosylate of H-Leu-OPac in 50 ml of DMF are added at −10° C., and then a solution of 4.80 g of NMM in 5 ml of DMF are added at −10° C. in a period of 1 hr. The reaction mixture is stirred at −10° C. for 3 hrs and then at ambient temperature for 3 hrs. The reaction mixture is poured into 300 ml of AcOEt. The organic phase is washed with a 5% aqueous solution of citric acid, with a 5% aqueous solution of sodium bicarbonate, with a saturated solution of sodium chloride. The organic phase is dried over MgSO$_4$ and evaporated to dryness. The residue is filtered and washed with petroleum ether and dried.

Yield: 29.4 g (100%), m.p.: 61°–70° C.
$[\alpha]_D^{20} = -39.9°$ (C=1, MeOH)

(B) 200 g of tosylate of H-Leu-OPac and 199 g of Boc-Lys(Z)-OH and 70.6 g of HOBt are dissolved in 1.2 l of DMF. To this solution 81.1 g of WSC are added at −10° C. The reaction mixture is stirred at −10° C. for 6 hrs (the end of the reaction is determined by HPLC).

The reaction mixture is poured into 1.2 l of AcOEt, and 1 l of a 20% aqueous solution of sodium chloride. After stirring for 15 mins, the organic phase is washed by:

1 l of a 5% aqueous solution of citric acid
1 l of a 10% aqueous solution of sodium bicarbonate
1 l of a water.

The organic phase is dried over MgSO$_4$ and filtered. The filterate is evaporated to dryness. The redidue is dissolved in 400 ml of AcOEt and the product is precipitated by addition of 1.2 l of n-hexane. It is drained and washed with n-hexane and dried.

Yield: 268 g (92.4%)

2. TosOH·H-Lys(Z)-Leu-Opac (BN−2)

27.0 g of BP-2 are dissolved in 300 ml of acetonitrile, and 16.8 g of TosOH·H$_2$O are added. The reaction mixture is stirred at ambient temperature for 3 hrs. The precipitate obtained is drained. The fitrate is evaporated to dryness. The residue is drained and washed with petroleum ether. Both precipitates are collected and dried.

Yield: 28.7 g (94.9%), m.p.: 139°–143° C.
$[\alpha]_D^{20} = -16.3°$ (C=1, MeoH)

3. PMZ-Arg(Mts)-Lys(Z)-Leu-OPac (BP'-3)

37.8 g of PMZ-Arg(Mts)-OH·CHA are dissolved in 500 ml of AcOEt and 200 ml of a 5% aqueous solution of citric acid. The organic phase is dried over MgSO$_4$ and evaporated to dryness. The residue are dissolved in 100 ml of THF and 5.69 g of NMM are added, and then 8.35 g of SBCF are added at −10° C. in the course of 15 mins. To this solution, a solution of 32.1 g of BN-2 and 4.74 g of NMM in 20 ml of DMF and 30 ml of THF are added with cooling in the course of 15 mins. The reaction mixture is stirred at ambient temperature for 3 hrs, and poured into 500 ml of AcOEt and 200 ml of water. The organic phase is washed with a 5% aqueous solution of citric acid, with a 5% aqueous solution of sodium bicarbonate, with a saturated solution of sodium chloride. The organic phase is dried over MgSO$_4$ and evaporated. The residue is filtered and washed with petroleum ether.

Yield: 46.1 g (96.9%), m.p.: 106°–107° C.
$[\alpha]_D^{20} = -24.3°$ (C=1, MeOH)

4. Boc-Arg(Mts)-Lys(Z)-Leu-OPac (BP-3)

Boc-Arg(Mts)-OH prepared from 218.24 g of Boc-Arg(MHs)-OH·CHA are dissolved in 600 ml of AcOEt at −10° C., 39.67 g of NMM, then 53.81 g of SBCF are added. The medium is stirred at −10° C. for 30 mins.

On the other hand, 200 g of BP-2 are suspended in 830 ml of acetonitrile at ambient temperature, 186.78 g of Tos-OH·H$_2$O are added. The medium is stirred at ambient temperature for 1 hr 30 mins. To this solution, 220 ml of DMF and 99.18 g of Et$_3$N are added at a temperature lower than 15° C.

This solution is added to the preceding solution containing the mixed anhydride of Boc-Arg(Mts)-OH at −10° C. The reaction mixture is stirred at −10° C. for 30 mins. To this solution 9.92 g of Et$_3$N are added and stirring is continued at −10° C. The reaction is terminated after 30 mins. The reaction mixture is poured into 1.3 l of AcOEt and 650 ml of a 10% aqueous solution of sodium chloride. The organic phase is washed with:

a 5% aqueous solution of citric acid
an 8% aqueous solution of sodium bicarbonate
a 25% aqueous solution of sodium chloride.

The organic phase is dried over MgSO$_4$ and filtered. The filtrate is evaporated to dryness. The residue is dissolved in 1.3 l of AcOEt and the product is precipitated by addition of 2.6 l of toluene and 5.2 l of n-hexane. It is drained and washed with n-hexane (1 l×2) and dried.

Yield: 297.6 g (95.7%), m.p.: 100°–107° C.
$[\alpha]_D^{20} = -25.1°$ (C=1, MeOH)

5. Boc-Ala-Arg(Mts)-Lys(Z)-Leu-OPac (BP-4)

(A) 19.7 g of BP'-3 are suspended in 20 ml of methylene chloride and 5 ml of anisole. To this mixture 20 ml of TFA are added with cooling in an ice bath. The reaction mixture is stirred for 1 hr and is evaporated. The residue is precipitated with diethyl ether, drained and dried. This powder are dissolved in 50 ml of DMF and neutralized by addition of 2.35 g of NMM.

On the other hand, 4.76 g of Boc-Ala-OH are dissolved in 100 ml of AcOEt and 2.35 g of NMM, then 3.19 g of SBCF are added at −10° C. in a period of 15 mins. To this solution, the preceding solution containing H-Arg(Mts)-Lys(Z)-Leu-OPac are added with cooling in a period of 30 mins. The reaction mixture is stirred for 3 hrs at ambient temperature and is poured into 200 ml of AcOEt and 100 ml of water. The organic phase is washed with a 5% aqueous solution of citric acid, with a 5% aqueous solution of sodium bicarbonate, with a saturated solution of sodium chloride. The organic phase is dried over MgSO$_4$ and evaporated. The residue is filtered and washed with petroleum ether.

Yield: 17.2 g (86.9%), m.p.: 100°–104° C.
$[\alpha]_D^{20} = -39.4°$ (C=1, MeOH)

(B) From 90.0 g of BP-3 and 180.0 g of Tos-OH·H$_2$O and 21.49 g of Boc-Ala-OH and 15.57 g of SBCF by employing the same technique as the one described in example II-4, 86.1 g (89.0%) of BP-4 are obtained, after recrystallization in the AcOEt-hexane mixture in the form of a white solid.

m.p.: 105°–110° C., $[\alpha_D^{20} = -36.0°$(C=1, MeOH)

6. Boc-Ser(Bzl)-Ala-Arg(Mts)-Lys(Z)-Leu-OPac (BP-5)

8.31 g of BP-4 are dissolved in 25 ml of acetonitrile and 15.5 g of TosOH·H$_2$O are added. This mixture is stirred at ambient temperature for 2 hrs and neutralized by addition of 8.22 g of NMM.

On the other hand, 2.88 g of Boc-Ser(Bzl)-OH are dissolved in 10 ml of THF, and 0.99 g of NMM, then 1.34 g of SBCF are added at −10° C. After stirring for 15 mins, the preceding solution containing H-Ala-Arg(Mts)-Lys(Z)Leu-OPac are added in a period of 15 mins. The reaction mixture is stirred at ambient temperature for 3 hrs, and is poured into 300 ml of AcOEt and 100 ml of water. The organic phase is washed with:
- a 5% aqueous solution of citric acid
- a 5% aqueous solution of sodium bicarbonate
- water.

The organic phase is evaporated. The residue is filtered and washed with diethyl ether.

Yield: 10.5 g (89.7%), m.p.: 120°–123° C.
$[\alpha]_D^{20} = -28.7°$ (C=1, MeOH)

7. Boc-Leu-Ser(Bzl)-Ala-Arg(Mts)-Lys(Z)-Leu-OPac (BP-6)

7.5 g of BP-5 are suspended in 50 ml of acetonitrile, and 11.8 g of TosOH·H$_2$O are added. This mixture is stirred at ambient temperature for 1 hr and neutralized by addition of 6.32 g of NMM.

On the other hand, 1.87 g of Boc-Leu-OH·H$_2$O is dissolved in 5 ml of AcOEt and dried over MgSO$_4$. To this solution 0.75 g of NMM and 1.03 g of SBCF are added at −10° C. After stirring for 15 mins, the preceding solution containing H-Ser(Bzl)-Ala-Arg(Mts)-Lys(Z)-Leu-OPac are added in a period of 15 mins. The reaction mixture is stirred at ambient temperature for 3 hrs, and is poured into 300 ml of AcOEt and 100 ml of water. The organic phase is washed with a 5% aqueous solution of citric acid, with a 5% aqueous solution of sodium bicarbonate, with a water. The organic phase is evaporated. The residue is filtered and washed with diethyl ether.

Yield: 6.98 g (85.0%), m.p.: 164°–165° C.
$[\alpha_D^{20} = -27.8°$ (C=1, MeOH)

8. Boc-Gln-Leu-Ser(Bzl)-Ala-Arg(Mts)-Lys(Z)-Leu-OPac (BP-7)

(A) 5.00 g of BP-6 are suspended in 50 ml of acetonitrile and 7.24 g of TosOH·H$_2$O are added. After stirring for 1 hr, the reaction mixture is neutralized by addition of 3.84 g of NMM, and is evaporated. The residue are dissolved in 10 ml of DMF and 2.80 g of Boc-Gln-ONp are added. The pH of the mixture is adjusted between 7 and 8 by addition of NMM and stirring is continued at ambient temperature for 16 hrs. The reaction mixture is poured into 200 ml of water. The precipitate obtained is drained. This crude product is washed with 200 ml of AcOEt with stirring at 50° C. for 30 mins. The precipitate obtained is drained and dried.

Yield: 4.57 g (83.2%), m.p.: 204°–208° C.
$[\alpha]_D^{20} = -20.1°$ (C=1, DMSO)

(B) 90.0 g of BP-6 are suspended in 840 ml of acetonitrile at ambient temperature, then 130.4 g of TosOH·H$_2$O are added. The reaction mixture is stirred at ambient temperature for 1 hr (the end of the reaction is determined by HPLC). To this solution are successively added at 5° C.: 69.34 g of Et$_3$N, 140 ml of DMF, 11.12 g of HOBt, 30.23 g of Boc-Gln-ONp, 6.93 g of Et$_3$N.

The reaction mixture is stirred at ambient temperature and the development of the reaction is followed by HPLC. The reaction is terminated after 2 hrs. The reaction mixture is poured into 2 l of water. After stirring for 30 mins, the precipitate obtained is filtered and washed with water (1 l) and dried.

Yield: 128.2 g

9. Boc-Gln-Leu-Ser(Bzl)-Ala-Arg(Mts)-Lys(Z)-Leu-OH (BC-7)

(A) 3.50 g of BP-7 are dissolved in 50 ml of acetic acid and 3.0 g of zinc powder are added. The reaction mixture is stirred at ambient temperature for 2 hrs. An insoluble substance is filtered and the filtrate is evaporated. The residue is taken up with water. The precipitate obtained is drained and dried.

Yield: 3.07 g (95.5%), m.p.: 192°–194° C.
$[\alpha]_D^{20} = -14.3°$ (C=1, DMSO)

(B) 50 g of BP-7 are dissolved in 330 ml of acetic acid at ambient temperature, then 45.4 g of zinc powder are added with cooling by an ice bath. The ice bath is removed and stirring is continued at ambient temperature for 1 hr 30 mins. An insoluble substance is filtered and the filtrate is poured into 2.2 l of water. The precipitate formed is drained and washed with water and dried. This product is washed again with 350 ml of AcoEt with stirring for 30 mins at 50° C. The solid is drained, washed with AcOEt and dried.

Yield: 34.5 g (75.1%)

EXAMPLE III Synthesis of PMZ-Arg(Mts)-Lys(Z)-Val-Leu-Gly-OH (CC'-5)

1. Boc-Leu-Gly-OPac (CP-2)

16.7 g of Boc-Leu-OH·H$_2$O is dissolved in 400 ml of AcOEt and 200 ml of a saturated aqueous solution of sodium chloride. The organic phase is washed with a saturated aqueous solution of sodium chloride and dried over MgSO$_4$ and filtered. The filtrate is evaporated to dryness. The residual oil is dissolved in 100 ml of DMF at ambient temperature, 23.3 g of tosylate of H-Gly-OPac, then 9.0 g of HOBt are added. To this solution 10.4 g of WSC is added at −15° C. The reaction mixture is stirred at −15° C. for 3 hrs, and at ambient temperature for 24 hrs. The reaction mixture is poured into 500 ml of toluene and 300 ml of water. The organic phase is washed by:
- water
- a 5% aqueous solution of sodium bicarbonate
- a 5% aqueous solution of citric acid
- a saturated solution of sodium chloride.

The organic phase is dried over Mg$_2$SO$_4$ and filtered. The filtrate is evaporated to dryness. The residue is dissolved in 100 ml of diethyl ether. By addition of 400 ml of hexane with stirring, the precipitate is obtained. It is drained and washed with hexane and dried.

Yield: 24.2 g (93.5%), m.p.: 108°–110° C.
$[\alpha]_D^{20} = -29.5°$ (C=1, MeOH)

2. Boc-Val-Leu-Gly-OPac (CP-3)

(A) 18.9 g of CP-2 is dissolved in 190 ml of acetonitrile and 35.4 g of TosOH·H$_2$O are added. The medium is stirred at ambient temperature for 1 hr 30 mins. The medium is evaporated to dryness. The residue is dissolved in 90 ml of THF and 19.6 ml of Et$_3$N are added with colling by an ice bath. To this solution are successively added at 0° C.:
- 6.9 g of HOBt
- 11.1 g of Boc-Val-OH
- 8.0 g of WSC The mixture is stirred at 0° C. for 2 hrs and at ambient temperature for 24 hrs. To this mixture, 500 ml of AcOEt and 300 ml of water are added. The organic phase is washed by:

water
a 5% aqueous solution of sodium bicarbonate
a 5% aqueous solution of citric acid
a saturated aqueous solution of sodium chloride.

The organic phase is evaporated to dryness. The residue is taken up in 500 ml of petroleumether. The solid is drained and washed with petroleum ether and dried.

Yield: 22.0 g (93.6%), m.p.: 146°–147° C.
$[\alpha]_D^{20} = -54.8°$ (C=1, MeOH)

(B) 145.3 g of CP-3 are obtained from 156.3 g of CP-2, 876.7 g of TFA, 739 g of Et$_3$N, 62.3 g of HOBt, 100.2 g of Boc-Val-OH, and 88.5 g of WSC by employing the same technique described in example-III-2(A) except the use of TFA instead of TosOH·H$_2$O as the deprotecting reagent of Boc.

Yield: 73.5%.

3. Boc-Lys(Z)-Val-Leu-Gly-OPac (CP-4)

(A) 21.5 g of CP-3 are dissolved in 66.5 ml of TFA at ambient temperature. The mixture is stirred at ambient temperature for 40 mins. To this mixture are successively added with cooling by an ice bath: 140 ml of THF, 113.3 ml of Et$_3$N, 6.3 g of HOBt, 17.8 g of Boc-Lys(Z)-OH, 50 ml of DMF, 7.3 g of WSC.

The reaction mixture is stirred at 0° C. for 2 hrs, and at ambient temperature for 24 hrs. The reaction mixture is poured into 1200 ml of AcOEt and 500 ml of water. The organic phase is washed by:
water
a 5% aqueous solution of sodium bicarbonate
a 5% aqueous solution of citric acid
a saturated aqueous solution of sodium chloride.

The organic phase is evaporated to dryness. The residue is taken up with 200 ml of diethyl ether and 400 ml of petroleum ether. The solid is filtered and washed with petroleum ether and dried. This product is suspended again in 200 ml of acetone with stirring at 40° C. for 30 mins. To this suspension 400 ml of diethyl ether are added. The solid is drained and dried.

Yield: 27.2 g (80.1%), m.p.: 189°–191° C.
$[\alpha]_D^{20} = -21.7°$ (C=1, DMF)

(B) 42.7 g (93.8%) of CP-4 are obtained from 30 g of CP-3, 57 g of methanesulfonic acid, 54 g of Et$_3$N, 8.8 g of HOBt, 24.8 g of Boc-Lys(Z)-OH and 10.1 g of WSC by employing the same technique described in example I-7.

4. PMZ-Arg(Mts)-Lys(Z)-Val-Leu-Gly-OPac (CP'-5)

5.5 g of CP-4 are dissolved in 11.3 ml of TFA. The reaction mixture is stirred at ambient temperature for 40 mins. To this mixture are successively added with cooling by an ice bath: 24 ml of THF, 20.2 ml of Et$_3$N, 1.1 g of HOBt, 4.5 g of PMZ-Arg(Mts)-OH, 24 ml of DMF, 1.2 g of WSC.

The reaction mixture is stirred at 0° C. for 2 hrs, then at ambient temperature for 24 hrs. The reaction mixture is concentrated. The residue is poured into 240 ml of water at a temperature lower than 5° C. The solid obtained is drained and washed with water, with diethyl ether in the solid state, then dried. This crude product is washed again with 40 ml of MeOH with stirring for 30 mins at 40° C. The solid is drained and dried.

Yield: 7.1 g (84.8%), m.p.: 200°–203° C.
$[\alpha]_D^{20} = -10.7°$ (C=1, DMF)

5. PMZ-Arg(Mts)-Lys(Z)-Val-Leu-Gly-OH (CC'-5)

4.9 g of CP'-5 are dissolved in 100 ml of acetic acid. To this solution 7.5 g of zinc powder in limited mounts is added at intervals of 10 mins. The reaction mixture is stirred for 3 hrs. An insoluble substance is filtered over celite and the filtrate is evaporated to dryness. The residue is taken up in 100 ml of diethyl ether. The solid is drained, washed with diethyl ether and dried.

Yield: 4.4 g (99.8%), m.p.: 195°–201° C.
$[\alpha]_D^{20} = -11.1°$ (C=1, DMF)

EXAMPLE IV Synthesis of Boc-Arg(Mts)-Lys(Z)-Val-Leu-Gly-OH (CC-5)

1. Boc-Arg(Mts)-Lys(Z)-Val-Leu-Gly-OPac (CP-5)

From 47 g of CP-4, 58.82 g of methansulfonic acid 55.74 g of Et$_3$N, 40.79 g of Boc-Arg(Mts)-OH.CHA, 9.92 g of HOBt and 11.39 g of WSC, 59.7 g (88.07%) of CP-5 are obtained by employing the same technique described in example I-7.

m.p.: 140°–147° C. $[\alpha]_D^{20} = -13.2°$ (C=1, DMF)

2. Boc-Arg(Mts)-Lys(Z)-Val-Leu-Gly-OH (CC-5)

From 49 g of CP-5 in 1012 ml of acetic acid and 8.67 g of zinc powder, 35.99 g (82.4%) of CC-5 are obtained by employing the same technique described in example III-5. m.p.: 198°–203° C.
$[\alpha]_D^{20} = -11.5°$ (C=1, DMF)

EXAMPLE V Synthesis of Boc-Tyr-Ala-Asp(OcHex)-Ala-Ile-Phe-Thr-Asn-Ser-Tyr-OH (FC-10)

1. Boc-Ser(Bzl)-Tyr(Bzl)-OBzl (DP-2)

(A) 25 g of tosylate of H-Tyr(Bzl)-OBzl are suspended in 50 ml of DMF and 4.74 g of NMM are added with stirring. On the other hand, 15.5 g of Boc-Ser(Bzl)-OH are dissolved in 50 ml of DMF and 5.31 g of NMM are added and then 7.17 g of isobutylchloroformate are added at −15° C. The mixture is stirred at −15° C. for 15 mins. To this mixture the preceding solution containing H-Tyr(Bzl)-OBzl is added at −15° C. during 10 mins. Stirring is continued whilst cooling the reaction mixture in an ice bath (1 hr) then at ambient temperature for 12 hrs. To this mixture, 600 ml of toluene and 300 ml of water are added. The organic phase is washed with a 5% aqueous solution of sodium bicarbonate, with a saturated aqueous solution of sodium chloride, and dried over Na$_2$SO$_4$ and evaporated to dryness. The residue is taken up in 400 ml of petroleum ether. The solid is filtered and washed with petroleum ether and dried.

Yield: 29.12 g (97.3%), m.p.: 79°–80° C.
$[\alpha]_D^{20} = -6.1°$ (C=1, MeOH)

(B) 120.7 g of DP-2 are obtained from 106.7 g of TosOH.H-Tyr(Bzl)-OBzl, 67.9 g of Boc-Ser(Bzl)-OH, 34.2 g of HOBt and 39.3 g of WSC by employing the same technique described in example II-1-(B) or III-1.

Yield: 94.5%

2. Boc-Asn-Ser(Bzl)-Tyr(Bzl)-OBzl (DP-3)

(A) 28.1 g of DP-2 are dissolved in 75.24 g of TFA with cooling in an ice bath. The reaction mixture is stirred at ambient temperature for 30 mins. To this mixture are successively added with cooling in an ice bath: 125 ml of DMF, 66.79 g of Et$_3$N, 11.24 g of Boc-Asn-OH, 7.19 g of HOBt, 10.21 g of WSC. Stirring is continued whilst cooling the reaction mixture in an ice bath (2 hrs) then at ambient temperature for 12 hrs. To the reaction mixture, 1 l of AcOEt and 300 ml of water are added. The organic phase is washed with a 5% aqueous solution of citiric acid, with a 5% aqueous solution of sodium bicarbonate and with water. The organic phase is evaporated to dryness. The residue is dissolved in the minimum of MeOH and the product is precipitated by addition of isopropylalcohol. The product is filtered, washed with isopropylalcohol, and dried. This product is recrystallized from isopropylalcohol. Yield: 28.0 g (84.5%) m.p.: 166°–167° C.

$[\alpha]_D^{20} = -16.7°$ (C=1, DMF) (B) From 133.2 g of DP-2, 100 g of methansulfonic acid, 84.4 g of Et$_3$N, 36.7 g of HOBt.H$_2$O, 55.7 g of Boc-Asn-OH and 37.2 g of WSC, 157 g (100%) of DP-3 are obtained by employing the same technique described in example I-7.

3. Boc-Thr(Bzl)-Asn-Ser(Bzl)-Tyr(Bzl)-OBzl (DP-4)

(A) 7.53 g of DP-3 are dissolved in 22.8 g of TFA with cooling in an ice bath. The reaction mixture is stirred at ambient temperature for 30 mins. To this mixture are successively added with cooling in an ice bath: 40 ml of DMF, 20.24 g of Et$_3$N, 3.4 g of Boc-Thr(Bzl)OH, 1.64 g of HOBt, 2.32 g of WSC. Stirring is continued whilst cooling the reaction mixture in an ice bath (2 hrs) then at ambient temperature for 12 hrs. The reaction mixture is poured into 250 ml of water at a temperature lower than 5° C. The solid formed is filtered, washed with water and dried. This crude product is crushed finely with a mortar and then is washed with 150 ml of acetonitrile with stirring for 1 hr. The solid is filtered and dried.

Yield: 8.06 g (85.4%), m.p.: 140°–143° C.
$[\alpha]_D^{20} = -6.7°$ (C=1, DMF)

(B) From 157 g of DP-3, 150 g of methanesulfonic acid, 137.1 g of Et$_3$N, 38.6 g of HOBt.H$_2$O, 74.2 g of Boc-Thr(Bzl)-OH and 39.2 g of WSC, 161.8 g (82.2%) of DP-4 are obtained by employing the same technique described in example I-7.

4. Boc-Phe-Thr(Bzl)-Asn-Ser(Bzl)-Tyr(Bzl)-OBzl (DP-5)

(A) 27.38 g of DP-4 are dissolved in 66.12 g of TFA with cooling in an ice bath. The reaction mixture is stirred at ambient temperature for 30 mins. To this solution are successively added with cooling in an ice bath: 200 ml of DMF, 58.69 g of Et$_3$N, 12.33 g of Boc-Phe-ONp. The pH of the mixture is adjusted between 7 and 8 by addition of Et$_3$N and it is stirred at ambient temperature for 24 hrs. The reaction mixture is poured into 1 l of water at a temperature lower than 5° C. The solid obtained is drained, washed with water and dried. This crude product is crushed finely with a mortar and then is washed with 260 ml of MeOH with stirring for 1 hr. The solid is drained and dried.

Yield: 25.81 g (81.6%), m.p.: 197°–199° C.
$[\alpha]_D^{20} = +1.3°$ (C=1, DMF)

(B) From 70.0 g of DP-4, 53.5 g of MSA, 48.8 g of Et$_3$N, 13.7 g of HOBt.H$_2$O, 21.6 g of Boc-Phe-OH and 13.9 g of WSC, 74.8 g of DP-5 are obtained by employing the same technique described in example I-7.
Yield: 92.0%

5. H-Phe-Thr(Bzl)-Asn-Ser(Bzl)-Tyr(Bzl)-OBzl (DN-5)

(A) 91.74 g of DP-5 are suspended in 233 ml of CH$_3$CN at ambient temperature, then a solution of 81.1 g of MSA in 50 ml of CH$_3$CN are added at 0° C. The reaction mixture is stirred at 0° C. for 1 hr 10 mins. To this mixture 244 ml of DMF and 102.5 g of Et$_3$N are added with cooling in an ice bath. After stirring for 30 mins, the mixture is poured into 4.2 l of water. The precipitate obtained is filtered and washed with water and dried in vacuum.

Yield: 83.28 g (99.95%)

(B) 3.27 g of DP-5 are suspended in 30 ml of acetonitrile and 8.56 g of TosOH.H$_2$O are added with cooling in an ice bath. The reaction mixture is stirred at ambient temperature for 30 mins. To this mixture, 4.86 g of Et$_3$N are added and then 150 ml of water are added with cooling by an ice-NaCl. The solid formed is drained and washed with water, with MeOH and dried.

Yield: 2.76 g (92.85%)

6. Boc-Ala-Ile-OBzl (EP-2)

23.61 g of tosylate of H-Ile-OBzl and 11.35 g of Boc-Ala-OH are suspended in 500 ml of AcOEt. To this mixture 6.07 g of Et$_3$N and 8.92 g of HOBt and then 12.65 g of WSC are added with cooling in an ice bath. Stirring is continued whilst cooling the reaction mixture in an ice bath (2 hrs) then at ambient temperature for 15 hrs. To this mixture a 5% aqueous solution of citric acid is added. The organic phase is washed with a 5% aqueous solution of sodium bicarbonate, with a saturated aqueous solution of sodium chloride. The organic phase is dried over Na$_2$SO$_4$ and evaporated to dryness. The oily product is obtained.

Yield: 24.2 g (102.8%)

7. Boc-Asp(OcHex)-Ala-Ile-OBzl (EP-3) (A) 21.77 g of EP-2 are dissolved in 61.56 g of TFA with cooling in an ice bath. The reaction mixture is stirred at ambient temperature for 1 hr. To this solution are successively added with cooling in an ice bath: 180 ml of THF, 54.64 g of Et$_3$N, 17.03 g of Boc-Asp(OcHex)-OH, 8.03 g of HOBt, 11.39 g of WSC. Stirring is continued whilst cooling the reaction mixture in an ice bath (2 hrs) then at ambient temperature for 16 hrs. To the reaction mixture, 540 ml of toluene and a 5% aqueous solution of citric acid are added. The organic phase is washed with a 5% aqueous solution of sodium bicarbonate, with a saturated aqueous solution of sodium chloride. The organic phase is dried over sodium sulfate and evaporated to dryness. The oily product is obtained.

Yield: 35.85 g (112.6%)

(B) From 172 g of EP-2, 242 g of TosOH.H$_2$O, 85.6 g of Et$_3$N, 63 g of HOBt, 147 g of Boc-Asp(OcHex)-OH and 72.3 g of WSC, 255 g (102%) of EP-3 are obtained by employing the same technique described in example I-2.

8. Boc-Ala-Asp(OcHex)-Ala-Ile-OBzl (EP-4)

(A) 35.85 g of EP-3 are dissolved in 61.56 g of TFA with cooling in an ice bath. The reaction mixture is stirred at ambient temperature for 1 hr. To this solution are successively added with cooling in an ice bath: 180 ml of THF, 54.64 g of Et$_3$N, 11.24 g of Boc-Ala-OH, 8.03 g of HOBt, 11.39 g of WSC. Stirring is continued whilst cooling the reaction mixture in an ice bath (2 hrs), then at ambient temperature for 15 hrs. To the reaction mixture, 900 ml of AcOEt and a 5% aqueous solution of citric acid are added. The organic phase is washed with a 5% aqueous solution of sodium bicarbonate, with a saturated aqueous solution of sodium chloride. The organic phase is dried over sodium sulfate and evaporated to dryness. The solid is obtained. This solid is recrystallized from 80 ml of AcOEt and 540 ml of n-hexane.

Yield: 30.11 g (84.4% from TosOH.H-Ile-oBzl) m.p.: 142°–146° C., $[\alpha]_D^{20} = -49.9°$ (C=1, MeOH)

(B) From 255 g of EP-3, 242 g of TosOH.H$_2$O, 85.6 g of Et$_3$N, 88.2 g of Boc-Ala-OH, 63.0 g of HOBt and 72.3 g of WSC, 226 g of EP-4 are obtained by employing the same technique described in example I-4.

Yield: 80.6%

9. Boc-Tyr(Bzl)-Ala-Asp(OcHex)-Ala-Ile-OBzl (EP-5)

(A) 29.08 g of EP-4 are dissolved in 75.24 g of TFA with cooling in an ice bath. The reaction mixture is stirred at ambient temperature for 1 hr. To this mixture are successively added with cooling in an ice bath: 190 ml of THF, 66.79 g of Et$_3$N, 20.59 g of Boc-Tyr(Bzl)-ONp. The pH of the mixture is adjusted between 7 and 8 by addition of Et$_3$N and stirring is continued at ambient temperature for 24 hrs. The reaction mixture is poured into 2 l of water at a temperature lower than 5° C. The solid obtained is filtered and washed with water and dried. This crude product is dissolved in 800 ml of MeOH and the product is precipitated by addition of 400 ml of water. The product is filtered and dried.

Yield: 38.06 g (94.6%), m.p.: 151°–153° C.
$[\alpha]_D^{20} = -32.6°$ (C=1, MeOH)

(B) From 58.0 g of EP-4, 66.7 g of TosOH.H$_2$O, 26.5 g of Et$_3$N, 35.7 g of Boc-Tyr(Bzl)-OH, 13.0 g of HOBt and 14.9 g of WSC, 80.0 g (100%) of EP-5 are obtained by employing the same technique described in example I-5.

10. Boc-Tyr-Ala-Asp(OcHex)-Ala-Ile-OH (EC-5)

A solution of 27.59 g of EP-5 in 140 ml of DMF; 270 ml of MeOH and 7 ml of acetic acid is hydrogenated for 10 hrs in the presence of 3.7 g of 10% Pd/C. The catalyst is filtered over celite and the filtrate is evaporated to dryness. The oily residue is taken up in diethyl ether. The solid obtained is drained and washed with diethyl ether and dried.

Yield: 19.34 g (87.3%), m.p.: 143°–155° C.
$[\alpha]_D^{20} = -10.1°$ (C=1, DMF)

11. Boc-Tyr-Ala-Asp(OcHex)-Ala-Ile-Phe-Thr(Bzl)-Asn-Ser(Bzl)-Tyr(Bzl)-OBzl (FP-10)

(A) 2.73 g of DN-5 are dissolved in 42 ml of DMF, 2.42 g of EC-5 then 0.456 g of HOSu are added. To this mixture 0.615 g of WSC are added with cooling in an ice bath. The reaction mixture is stirred with cooling in an ice bath for 2 hrs and then at ambient temperature for 24 hrs. The reaction mixture is poured into 150 ml of water at a temperature lower than 5° C. The solid obtained is drained, washed with water and dried. This crude product is crushed finely with a mortar and then is washed with 100 ml of MeOH with stirring at 50° C. for 30 mins. The solid is drained and dried. This solid is reprecipitated from DMF/MeOH.

Yield: 2.51 g (53.5%), m.p.: 235°–237° C.
$[\alpha]_D^{20} = -0.9°$ (C=1, DMSO)

(B) 15.00 g of DN-5 are dissolved in 105 ml of DMF, and 13.32 g of EC-5, then 2.70 g of HOBt are added at 25° C. To this solution 3.84 g of WSC.hydrochloride are added at −10° C. and stirred for 2 hrs 20 mins at same temperature. 459 mg of NMM are added at −10° C. After stirring for 1 hr at −10° C., 459 mg of NMM are added and stirring is continued for 1 hr at −10° C. The reaction mixture is poured into 2.25 l of water at 0° C. The precipitate obtained is filtered and washed with water and dried in vacuum. This crude product is suspended in 600 ml of MeOH. After stirring for 1 hr at ambient temperature, the solid obtained is filtered and washed with MeOH and dried.

Yield: 24.08 g (93.2%)

12. Boc-Tyr-Ala-Asp(OcHex)-Ala-Ile-Phe-Thr-Asn-Ser-Tyr-OH (FC-10)

A solution of 1.8 g of FP-10 in 120 ml of DMF and 9 ml of acetic acid is hydrogenated for 11 hrs in the presence of 0.9 g of 10% Pd/C. The catalyst is filtered over celite and the filtrate is evaporated to dryness. The oily residue is taken up in diethyl ether. The solid obtained is filtered and washed with diethyl ether and dried.

Yield: 1.32 g (93.4%), m.p.: 213°–215° C.
$[\alpha]_D^{20} = -0.4°$ (C=1, DMSO)

EXAMPLE VI

Synthesis of Boc-Ile-Phe-Thr-Asn-Ser-Tyr-OH (DC-6)

1. Boc-Ile-Phe-Thr(Bzl)-Asn-Ser(Bzl)-Tyr(Bzl)-OBzl (DP-6)

44.7 g of DP-5 are suspended in 270 ml of acetonitrile and a solution of 39.4 g of methane sulfonic acid in 138 ml of acetonitrile are added at −5° C. The reaction mixture is stirred at ambient temperature for 1 hr. To this solution are successively added with cooling in an ice bath: 480 ml of DMF, 37.3 g of Et$_3$N, 6.70 g of HOBt, 10.82 g of Boc-Ile-OH.½H$_2$O, 7.7 g of WSC. Stirring is continued whilst cooling the reaction mixture in an ice bath (30 mins) then at ambient temperature for 2 hrs 30 mins.

The reaction mixture is poured into 4.8 l of water with cooling in an ice bath. The precipitate obtained is drained and washed with water and dried. 50.8 g of the crude product is obtained. 50.8 g of the crude product are suspended in 740 ml of acetonitrile and stirred at ambient temperature for 1 hr. The precipitate is drained and washed with acetonitrile and dried.

Yield: 45.4 g (92%), m.p.: 210°–211° C.
$[\alpha]_D^{20} = -2.0°$ (C=1.1, DMF)

2. Boc-Ile-Phe-Thr-Asn-Ser-Tyr-OH (DC-6)

A solution of 40.1 g of DP-6 in 1200 ml of DMF and 600 ml of acetic acid is hydrogenated at 40° C. for 5 hrs in the presence of 40.4 g of 5% Pd-C. The catalyst is filtered over celite and the filtrate is evaporated to dryness. The oily residue is taken up with diethyl ether. The solid obtained is drained and washed with diethyl ether and dried.

Yield: 22.7 g (80.7%), m.p.: 199° (decomposition)

$[\alpha]_D^{20} = +1.9°$ (C=1.1, DMF)

EXAMPLE VII

Synthesis of Boc-Tyr(Cl$_2$-Bzl)-Ala-Asp(OBzl)-Ala-OH (KC-4)

1. Boc-Asp(OBzl)-Ala-OPac (KP-2)

100 g of tosylate of H-Ala-OPac, and 93.7 g of Boc-Asp(OBzl)-OH, and 39.2 g of HOBt are dissolved in 750 ml of DMF. To this solution 45.0 g of WSC are added at −10° C. in a period of 1 hr 30 mins. The reaction mixture is stirred at −10° C. for 1 hr and is poured into 1 l of AcOEt and 600 ml of a saturated solution of sodium chloride. The organic phase is washed with a 5% aqueous solution of citric acid, with an 8% aqueous solution of sodium bicarbonate and with a water. The organic phase is dried over MgSO$_4$ and evaporated. The residue is filtered and washed with hexane.

Yield: 114 g (84.4%), m.p.: 107°–109° C.
$[\alpha]_D^{20} = -36.7°$ (C=1, MeOH)

2. Boc-Ala-Asp(OBzl)-Ala-OPac (KP-3)

40.0 g of KP-2 are dissolved in 240 ml of acetonitrile and 59.3 g of TosOH.H$_2$O are added. The reaction mixture is stirred at ambient temperature for 1 hr and neutralized by 31.5 g of Et$_3$N at −10° C.

On the other hand, 16.2 g of Boc-Ala-OH are dissolved in 80 ml of AcOEt, and 8.66 g of NMM, then 11.8 g of SBCF are added at −10° C. in a period of 5 mins. After stirring for 15 mins, the preceding solution containing H-Asp(OBzl)-Ala-OPac are added at −10° C. in a period of 5 mins. The reaction mixture is stirred at ambient temperature for 3 hrs and is poured into 600 ml of AcOEt and 300 ml of a saturated solution of sodium chloride. The organic phase is washed with a 5% aqueous solution of citric acid, with an 8% aqueous solution of sodium bicarbonate, with a water. The organic phase is dried over MgSO$_4$ and evaporated. The solid obtained is recrystallized from AcOEt-hexane.

Yield: 42.6 g (93.6%), m.p.: 145°–147° C.
$[\alpha]_D^{20} = -51.0°$ (C=1, DMF)

3. Boc-Tyr(Cl$_2$-Bzl)-Ala-Asp(OBzl)-Ala-OPac (KP-4)

20.0 g of KP-3 are suspended in 200 ml of acetonitrile and 26.0 g of TosOH.H$_2$O are added. The reaction mixture is stirred at ambient temperature for 1 hr and neutralized by 13.8 g of Et$_3$N at −10° C.

On the other hand, 16.6 g of Boc-Tyr(Cl$_2$-Bzl)-OH are dissolved in 50 g of THF, and 3.80 g of NMM, then 5.16 g of SBCF are added at −10° C. in a period of 15 mins. After stirring for 15 mins, the proceding solution containing H-Ala-Asp(OBzl)-Ala-OPac are added at −10° C. in a period of 15 mins. The reaction mixture is stirred at ambient temperature for 3 hrs and is poured into 500 ml of AcOEt and 200 ml of a saturated solution of sodium chloride. The organic phase is washed with an 8% aqueous solution of sodium bicarbonate, with a water. The organic phase is dried over MgSO$_4$ and filtered. 500 ml of hexane are added to the filtrate. The precipitate obtained is drained and washed with hexane.

Yield: 25.0 g, m.p.: 174°–176° C. $[\alpha]_D^{20} = -20.7°$ (C=1, DMF)

4. Boc-Tyr(Cl$_2$-Bzl)-Ala-Asp(OBzl)-Ala-OH (KC-4)

20.0 g of KP-4 are dissolved in 240 ml of acetic acid, and 28.9 g of zinc powder are added. The reaction mixture is stirred at ambient temperature for 1 hr. An insoluble substance is filtered and the filtrate is evaporated. The residue is taken up with water. The solid obtained is drained and dried. This crude product is recrystallized from AcOEt-hexane.

Yield: 14.2 g (81.3%), m.p.: 132°–138°
$[\alpha]_D^{20} = -14.2°$ (C=1, DMF)

EXAMPLE VIII

Synthesis of Boc-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH$_2$ (IP-14)

1. H-Leu-Gln-Asp(OBzl)-Ile-Met(O)-Ser(Bzl)-Arg(Mts)-NH$_2$(AN-7)

(A) A solution of 5.0 g of AP-7 in 30 ml of TFA is stirred at ambient temperature for 1 hr. This solution is poured into 500 ml of water containing 54.2 ml of Et$_3$N. The precipitate obtained is filtered and washed with water and dried.

Yield: 4.55 g (98.3%), m.p.: 203°–210° C.
$[\alpha]_D^{20} = -7.0°$ (C=1, DMSO)

(B) From 13.0 g of AP-7, 18.6 g of MSA and 19.6 g of Et$_3$N, 11.9 g of AN-7 are obtained by employing the same technique described in example V-5-(A).

Yield: 99.2%

2. Boc-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH$_2$ (IP-14)

(A) 2.60 g of BC-7 are dissolved in 5 ml of DMF and 2.5 ml of DMSO, 2.54 g of AN-7 then 272 mg of HOSu are added. To this solution 486 mg of DCC are added. The pH of the mixture is adjusted between 7 and 8 by addition of NMM and it is stirred at ambient temperature for 24 hrs. The reaction mixture is poured into 50 ml of water. The solid obtained is drained. The solid is washed with 30 ml of MeOH with stirring at 50° C. for 30 mins. The solid obtained is drained and dried.

Yield: 4.16 g (81.6%), m.p.: 270°–271° C.
$[\alpha]_D^{20} = -17.2°$ (C=1, DMSO)

Analysis of amino acids Asp 1.04(1), Ser 1.88(2), Glu 1.02(1), Ala 1.00(1), Met 0.83(1), Ile 0.86(1), Leu 2.97(3), Lys 1.02(1), Arg 1.97(2). (average recovery 94.3%)

(B) 11.9 g of AN-7 are dissolved in 10 ml of DMF and 80 ml of DMSO, 12.7 g of BC-7 then 1.32 g of HOSu are added at ambient temperature. To this solution 2.19 g of TosOH.H$_2$O and 1.78 g of WSC are added at 25° C. The reaction mixture is stirred at 25° C. for 5 hrs. 970 mg of Et$_3$N are added to the reaction mixture. After stirring for 4 hrs, the reaction mixture is poured into 360 ml of water. The precipitate obtained is filtered and washed with water. This crude product is suspended in 250 ml of MeOH with stirring at 65° C. for 1 hr. The precipitate is filtered and washed with MeOH and dried in vacuum.

Yield: 18.8 g (77%)

EXAMPLE IX

Boc-Arg(Mts)-Lys(Z)-Val-Leu-Gly-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH$_2$ (IP-19)

18.8 g of IP-14 are added to a solution of 28.4 g of MSA in 120 ml of CH$_3$CN at 5° C. After stirring for 1 hr at 5° C., 130 ml of N-methylpyrolidone containing 29.9 g of Et$_3$N are added at 5° C. To this solution, 7.67 g of CC-5, 2.26 g of HOBt, and 1.37 g of WSC are added. The reaction mixture is stirred at ambient temperature for 6 hrs and is poured into 3 l of a 1% aqueous solution of sodium chloride. The precipitate obtained is filtered and washed with water and dried.

Yield: 25.2 g (100%), m.p.: 246° (decomposition)
$[\alpha]_D^{20} = -13.5°$ (C=1, DMSO)

EXAMPLE X

Synthesis of
PMZ-Arg(Mts)-Lys(Z)-Val-Leu-Gly-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH₂ (IP'-19)

1.
H-Gln-Leu-Ser(Bzl)-Ala-Arg(Mts)-Lys(Z)-Leu-Leu-Gln- Asp(OBzl)-Ile-Met(O)-Ser(Bzl)-Arg(Mts)-NH₂ (IN-14)

A solution of 3.50 g of IP-14 in 35 ml of TFA is stirred with cooling in an ice bath for 30 mins. This solution is poured into 500 ml of water containing 66 ml of Et₃N with cooling in an ice bath. The solid obtained is drained, washed with water and dried.

Yield: 3.31 g (98.2%), m.p.: 264°–267° C.
$[\alpha]_D^{20} = -21.9°$ (C=1, DMSO)

2.
PMZ-Arg(Mts)-Lys(Z)-Val-Leu-Gly-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH₂ (IP'-19)

1.87 g of CC'-5 and 325 mg of HOBt are dissolved in 20 ml of DMSO and 10 ml of DMF. To this solution, 372 mg of DCC and 3.0 g of IN-14 are added. The pH of the mixture is adjusted between 7 and 8 by addition of NMM and it is stirred at ambient temperature for 10 hrs. The reaction mixture is poured into 30 ml of water. The solid obtained is drained and washed with 30 ml of MeOH with stirring at 50° C. for 30 mins. The solid obtained is drained and dried.

Yield: 3.87 g (91.5%), m.p.: 275°–278° C.
$[\alpha]_D^{20} = -19.9°$ (C=1, DMSO)

Analysis of amino acids Asp 1.05(1), Ser 1.87(2), Glu 2.03(2), Gly 1.00(1), Ala 1.00(1), Val 0.75(1), Met 0.82(1), Ile 0.72(1), Leu 3.86(4), Lys 1.92(2), Arg 2.87(3) (average recovery 95.7%)

EXAMPLe XI

Synthesis of
Boc-Tyr-Ala-Asp(OcHex)-Ala-Ile-Phe-Thr-Asn-Ser-Tyr-Arg(Mts)-Lys(Z)-Val-Leu-Gly-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH-hd 2 (IP-29)

1.
H-Arg(Mts)-Lys(Z)-Val-Leu-Gly-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH₂ (IN-19)

(A) A solution of 3.50 g of IP'-19 in 15 ml of TFA and 5 ml of anisole is stirred with cooling in an ice bath for 30 mins. This solution is poured into 300 ml of water containing 28.4 ml of Et₃N with cooling in an ice bath. The solid obtained is drained and washed with MeOH and dried.

Yield: 3.03 g (89.1%), m.p.: 280°–283° C.
$[\alpha]_D^{20} = -25.0$ (C=1, DMSO)

(B) From 25.2 g of IP-19, 28.4 g of MSA and 29.8 g of Et₃N, 23.6 g of IN-19 are obtained by employing the same technique described in example V-5-(A).

Yield: 96.3%

2.
Boc-Tyr-Ala-Asp(OcHex)-Ala-Ile-Phe-Thr-Asn-Ser-Tyr-Arg(Mts)-Lys(Z)-Val-Leu-Gly-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH₂ (IP-29)

(A) 253 mg of IN-19 and 100 mg of FC-10 and 9.4 mg of HOSu are dissolved in 2 ml of DMSO and 1 ml of DMF. To this solution 16.8 mg of DCC are added. The reaction mixture is stirred for 2 days at ambient temperature, maintaining the pH at 7–8 by addition of NMM. The reaction mixture is poured into 10 ml of water. The precipitate obtained is drained and dried. This crude product is washed with 3 ml of MeOH with stirring at ambient temperature for 30 mins. The solid obtained is drained and dried.

Yield: 290 mg (82.3%), m.p.: 279°–283° C.
$[\alpha]_D^{20} = -14.0°$ (C=1, DMSO)

Analysis of amino acids Asp 2.84(3), Thr 0.88(1), Ser 2.81(3), Glu 1.98(2), Gly 1.01(1), Ala 3.00(3), Val 0.73(1), Met 0.82(1), Ile 1.78(2), Leu 3.75(4), Tyr 1.80(2), Phe 0.90(1), Lys 1.83(2), Arg 2.82(3) (average recovery 92.5%)

(B) 17.3 g of IN-19 are dissolved in 200 ml of N-methyl pyrolidone, 8.41 g of FC-10, then 1.12 g of HONB are added at 25° C. To this solution 0.965 g of WSC are added at 25° C. The reaction mixture is stirred for 15 hrs at 25° C. 2.2 l of water are added to this solution and stirred for 1 hr. The precipitate obtained is filtered and washed with water and dried.

Yield: 24.5 g (100%)

EXAMPLE XII

Synthesis of
Boc-Ile-Phe-Thr-Asn-Ser-Tyr-Arg(Mts)-Lys(Z)-Val-Leu-Gly-Gln-Leu-Ser(Bzl)-Ala-Arg(Mts)-Lys(Z)-Leu-Leu-Gln-Asp(OBzl)-Ile-Met(O)-Ser(Bzl)-Arg(Mts) NH₂ (IP-25)

735 mg of IN-19 and 281 mg of DC-6 and 92 mg of HOBt.H₂O are dissolved in 7.5 ml of DMSO and 7.5 ml of N-methylpyrolidone. To this solution 70 mg of WSC.hydrochloride are added with cooling in an ice bath. The reaction mixture is stirred for 24 hrs with cooling in an ice bath and is poured into 150 ml of water. After stirring for 30 mins, the precipitate is drained and washed with water and dried.

Yield: 769 mg (83.8%), m.p.: 128°–140° C.
$[\alpha]_D^{25} = -11.5°$ (C=1.1, DMSO)

Analysis of amino acids Asp 1.95(2), Thr 0.91(1), Ser 2.82(3), Glu 2.15(2), Gly 1.00(1), Ala 1.02(1), Val 0.95(1), Met 0.85(1), Ile 1.90(2), Leu 3.88(4), Tyr 1.12(1), Phe 1.07(1), Lys 2.16(2), Arg 2.96(3) (average recovery 94.5%)

EXAMPLE XIII

Boc-Tyr(Cl₂Bzl)-Ala-Asp(OBzl)-Ala-Ile-Phe-Thr-Asn-Ser-Tyr-Arg(Mts)-Lys(Z)-Val-Leu-Gly-Gln-Leu-Ser(Bzl)-Ala-Arg(Mts)-Lys(Z)-Leu-Leu-Gln-Asp(OBzl)-Ile-Met(O)-Ser(Bzl)-Arg(Mts)-NH₂ (IP'-29)

910 mg of IP-25 are dissolved in 3.39 ml of TFA with cooling in an ice bath. After stirring for 1 hr with cooling in an ice bath, 3.39 ml of DMF and 7.36 ml of Et₃N then 24 ml of water are added with cooling by iceNaCl. After stirring for 15 mins, the precipitate formed is drained and washed with water and dried.

Yield: 910 mg 910 mg of the solid obtained with the preceding treatment are dissolved in 4.5 ml of DMSO and 4.5 ml of N-methyl pyrolidone, and 173 mg of KC-4, and 67 mg of HOBt.H$_2$O are added. To this solution 46 mg of WSC.hydrochloride are added with cooling in an ice bath. The reaction mixture is stirred with cooling in an ice bath for 30 mins, then at ambient temperature for 2 hrs. 90 ml of water are added to the reaction mixture. The precipitate obtained is drained and washed with water and dried.

Yield: 936 mg (88.5%), m.p.: 130°–145° C.

$[\alpha]_D^{25} = -10.8°$ (C=1.0, DMSO)

Analysis of amino acids Asp 2.92(3), Thr 0.88(1), Ser 2.79(3), Glu 2.09(2), Gly 1.00(1), Ala 3.04(3), Val 0.92(1), Met 0.87(1), Ile 1.85(2), Leu 3.86(4), Tyr 2.13(2), Phe 1.04(1), Lys 2.06(2), Arg 2.88(3) (average recovery 92.3%)

EXAMPLE XIV

Synthesis of
H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH
(polypeptide (I))

(A) 100 mg of IP-29 are suspended in 150 μl of anisole and 25 μl of methylethylsulfide. To this mixture 5 ml of hydrogen fluoride are added with cooling by dry ice/EtOH. The reaction mixture is stirred at −20° C. for 30 mins and at 0° C. for 1 hr and then concentrated in vacuum. The residue is dissolved in 3 ml of TFA. This solution is poured into 20 ml of diethyl ether. The precipitate obtained is filtered and washed with diethylether and dried. This solid is dissolved in 5 ml of water containing 360 mg of N-methylmercaptoacetamide. The reaction mixture is stirred at 37° C. for 38 hrs. To this mixture 6 ml of n-butanol and 1 ml of EtOH are added and the pH of the mixture is adjusted to 9 by addition of 1N-sodium hydroxide and stirred for 30 mins. The organic phase is evaporated to dryness. The residue is taken up in 8 ml of acetonitrile. The solid obtained is drained and dried. This solid is dissolved in 1% aqueous acetic acid and subjected to a reverse phase chromatography (YMC-GEL ODS S-15/30) 10×250 mm. After the column is washed with water, with 0.1M AcONH$_4$ (pH 5.0), the product is eluted with 35% acetonitrile −65% 0.1M AcONH$_4$ (pH 5.0). The eluted fractions between 160 ml and 168 ml are collected together, evaporated and lyophilized. The lyophilizate thus obtained is dissolved again in 5 ml of water and lyophilized. (2 times) Yield: 37 mg. The preceding lyophilizate is dissolved in 8 ml of 1% acetic acid and subjected to a reverse phase chromatography (YMC-GEL ODS S-15/30) 10×250 mm. After the column is washed with 20 ml of 1% acetic acid, the product is eluted with 22% acetonitrile −78% 1% acetic acid. The eluted fractions between 153 ml and 160 ml are collected together, evaporated and lyophilized. Thus 23 mg of polypeptide (I) is obtained.

$[\alpha]_D^{20} = -67°$ (C=0.1, H$_2$O)

Analysis of amino acids Asp 2.88(3), Thr 0.92(1), Ser 2.71(3), Glu 1.96(2), Gly 1.00(1), Ala 3.00(3), Val 0.94(1), Met 0.98(1), Ile 1.97(2), Leu 3.82(4), Tyr 1.77(2), Phe 0.95(1), Lys 2.05(2), Arg 2.79(3) (average recovery 95.5%)

300 mg of IP′-29 are stirred for 2 hrs 30 mins with cooling in an ice bath in 1.8 ml of TFA containing 287 μl of m-cresole, 323 μl of thioanisole, 302 μl of trichloromethylsilane and 304 μl of TFMSA. 50 ml of diethyl ether is then added. The precipitate obtained is filtered, washed with diethyl ether. The product is dissolved in 90 ml of 5% acetic acid containing 9 ml of 2-mercaptoethanol. The pH of the mixture is adjusted at 9 by aqueous sodium hydroxide. After stirring for 1 hr, the pH is adjusted to 5 by acetic acid. This solution is subjected to a reverse phase chromatography (YMC-GEL ODS S-15/30) 20×300 mm. After the column is washed with water, with 0.1M AcONH$_4$ (pH 5.0), the product is eluted with 35% acetonitrile −65% 0.1M AcONH$_4$ (pH 5.0). The eluted fractions between 600 ml and 650 ml are collected and concentrated. This concentrated solution is applied to reverse phase chromatography (YMC-GEL ODS S-15/30) 20×300 mm. After the column is washed with 1% acetic acid, the product is eluted with 22% acetonitrile−78% 1% acetic acid. The eluted fractions between 700 ml and 800 ml are collected, evaporated and lyophilized. Thus, 56 mg of polypeptide (I) is obtained.

$[\alpha]_D^{20} = -65°$ (C=0.1, H$_2$O)

Analysis of amino acids Asp 2.96(3), Thr 0.93(1), Ser 2.75(3), Glu 1.95(2), Gly 1.00(1), Ala 3.06(3), Val 0.93(1), Met 0.97(1), Ile 1.86(2), Leu 3.85(4), Tyr 2.07(2), Phe 1.04(1), Lys 1.98(2), Arg 2.85(3) (average recovery 96.2%)

What is claimed is:

1. A process for the manufacture of a polypeptide (I) having the formula:

$$\underset{\phantom{H-Tyr-Ala-Asp-Ala-Ile-}5\phantom{Phe-Thr-Asn-Ser-}10}{} \quad (I)$$
H—Tyr—Ala—Asp—Ala—Ile—Phe—Thr—Asn—Ser—Tyr—

$$\underset{\phantom{Arg-Lys-Val-Leu-}15\phantom{Gly-Gln-Leu-Ser-}20}{}$$
Arg—Lys—Val—Leu—Gly—Gln—Leu—Ser—Ala—Arg—

$$\underset{\phantom{Lys-Leu-Leu-Gln-}25\phantom{Asp-Ile-Met-Ser-}29}{}$$
Lys—Leu—Leu—Gln—Asp—Ile—Met—Ser—Arg—NH$_2$ which comprises steps of:

(a) coupling, successively and in the order of the sequence of the polypeptide (I), four protected fragments A, B, C and D or five protected fragments A, B, C, E and F, said fragment A by the formula, Leu-Gln-Asp-Ile-Met-Ser-Arg-NH$_2$ said fragment B by the formula, Gln-Leu-Ser-Ala-Arg-Lys-Leu said fragment C by the formula, Arg-Lys-Val-Leu-Gly said fragment D by the formula, Tyr-Ala-Asp-Ala-Ile-Phe-Thr-Asn-Ser-Tyr said fragment E by the formula, Ile-Phe-Thr-Asn-Ser-Tyr and said fragment F by the formula, Tyr-Ala-Asp-Ala being represented, respectively, and (b) eliminating, at the end of sequence, all the protecting groups to provide the polypeptide (I).

2. The process of claim 1, wherein the coupling is carried out with aid of the carbodiimide reagent in the presence of additive.

3. A protected fragment comprising an amino acid sequence of the formula,
Arg-Lys-Val-Leu-Gly.

4. A protected fragment comprising an amino acid sequence of the formula,
Tyr-Ala-Asp-Ala-Ile-Phe-Thr-Asn-Ser-Tyr.

5. A protected fragment comprising an amino acid sequence of the formula,

Ile-Phe-Thr-Asn-Ser-Tyr.

6. A protected fragment comprising an amino acid sequence of the formula,

Boc-Tyr(Cl₂-Bzl)-Ala-Asp(OBzl)-Ala-OH.

7. A protected intermediate peptide comprising an amino acid sequence of the formula, Gln-Leu-Ser-Ala-Arg-Lys-Leu-Leu-Gln-Asp-Ile-Met-Ser-Arg-NH₂.

8. A solvent-soluble protected intermediate peptide comprising an amino acid sequence of the formula,

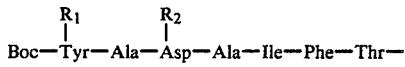

-continued

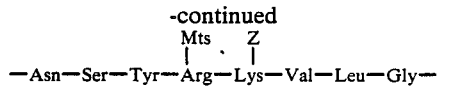

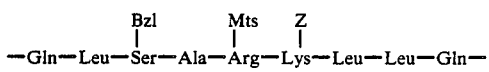

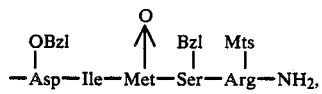

wherein R₁ is H or Cl₂Bzl and R₂ is OcHex or OBzl.

9. A protected intermediate peptide comprising an amino acid sequence of the formula, Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂.

* * * * *